United States Patent [19]

Shoher et al.

[11] Patent Number: 4,704,089
[45] Date of Patent: Nov. 3, 1987

[54] METHOD FOR CONSTRUCTING A DENTAL BRIDGE WITHOUT CASTING AND DENTAL PROSTHESIS

[76] Inventors: Itzhak Shoher, 50 ShlomoHamelech St., Tel-Aviv, Israel, 64386; Aharon E. Whiteman, 13 J. L. Perez St., Petach-Tikvah, Israel, 49206

[21] Appl. No.: 822,823

[22] Filed: Jan. 27, 1986

Related U.S. Application Data

[63] Continuation-in-part of Ser. No. 723,072, Apr. 15, 1985.

[51] Int. Cl.⁴ .............................................. A66C 13/24
[52] U.S. Cl. .................................................. 433/183
[58] Field of Search ......................... 432/182, 183, 181

[56] References Cited

U.S. PATENT DOCUMENTS 318,581   5/1885   Sheffield ............................ 433/183
4,431,417  2/1984  Weissman ........................... 433/182

Primary Examiner—Robert Peshock
Attorney, Agent, or Firm—E. Lieberstein

[57] ABSTRACT

A method and prosthesis assembly for fabricating a dental bridge to abutment teeth upon which metal retaining members have been mounted comprising suspending a pontic having non rigid arm rests extending from opposite ends thereof between the occlusal surfaces of the metal retaining members, adjusting the position of the arm rests to establish a desired alignment between the pontic and the abutment teeth, spot welding each arm rest to the occlusal surface of each retaining member to form a welded joint and soldering the interproximal space between each retaining member and the pontic. To facilitate the spot welding operation a metal spacer is interposed between the arm rest and the retaining member.

42 Claims, 11 Drawing Figures

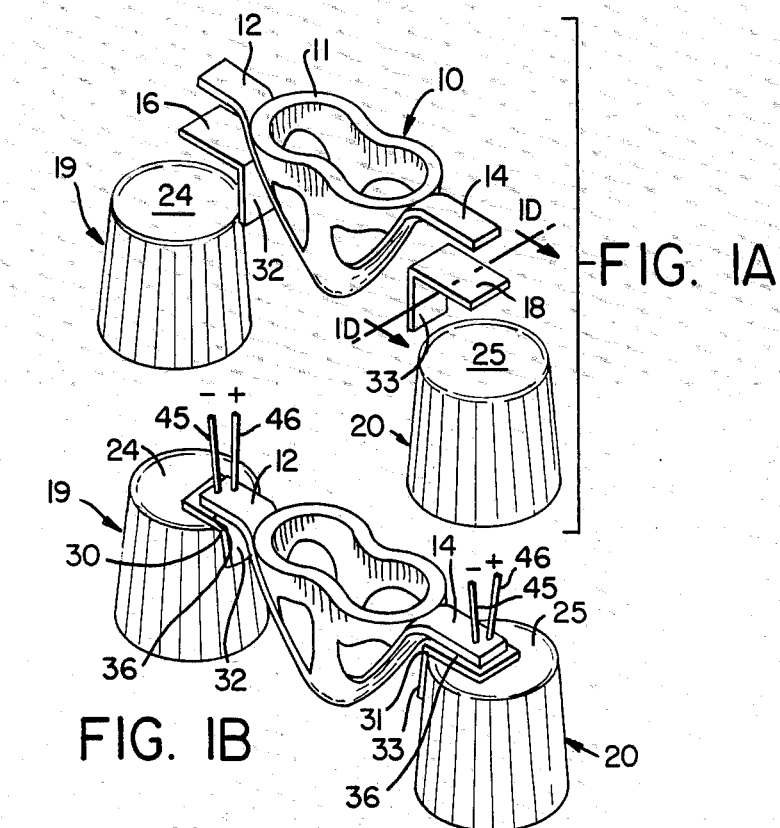
FIG. IA
FIG. IB
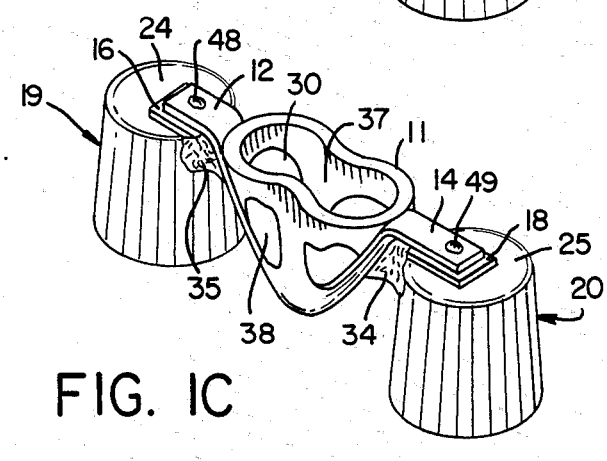
FIG. IC
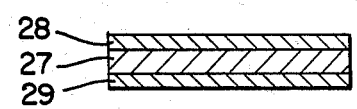
FIG. ID

METHOD FOR CONSTRUCTING A DENTAL BRIDGE WITHOUT CASTING AND DENTAL PROSTHESIS

The present invention is a continuation-in-part of U.S. Ser. No. 723072 filed Apr. 15, 1985, and entitled PREFABRICATED DENTAL PROSTHESIS. More particularly, the present invention relates to a method for constructing a dental bridge without casting and to a dental prosthesis assembly for fabricating a dental bridge without casting.

BACKGROUND OF THE INVENTION

Crown and bridge prosthodontics is the science and art of the complete restoration of one or more teeth and the replacement of one or more natural teeth with an artificial device. A bridge is used to replace at least one missing tooth and is supported by natural teeth. The bridge includes a pontic which fills the edentulous space between abutment teeth and a connector which joins the pontic to a bridge retaining member such as a crown formed on each abutment tooth adjacent the pontic.

The primary purpose of the dental bridge is to receive the forces of occlusion and to transmit them through the abutments so that occlusion is restored to the patient, thereby contributing to mastication. The bridge should also augment the ability of the patient to enunciate and maintain the position of the teeth relative to opposing teeth. The present day construction of a dental bridge is a time consuming, involved and complex process which requires the application of many independent procedures including the following: waxing, spruing;, investing, casting, cleaning, trimming, cutting and stoning. The process, as conventionally practiced, is referred to colloquially as the "lost wax casting method" and is currently the universally accepted procedure for making a bridge. The bridge retaining member(s) and pontic may be cast as one piece or each may individually be cast and joined by soldering. The preparation for casting and the casting process must be meticulously followed with the technician paying strict attention to detail, particularly during the wax-up, investment, spruing and casting operations to assure accuracy of the cast product and proper fit. If the fit is not accurate, it will, in most cases, be necessary to recast the bridge which substantially increases the time spent both by the dentist and dental technician in completing the restoration.

In the construction of a fixed bridge, it is customary to cast the bridge retaining member(s) and the pontic separately and then to unite the pontic to the retaining member(s) by a solder connection on an investment model. The strength of a dental bridge formed by soldering the bridge elements together is dependent upon the strength of the solder joint and the bond formed between the solder joint and bridge retainer. A bridge with a weak solder connection is susceptible to early failure.

It has been discovered in accordance with the present inventon that a pontic can be joined to a bridge retaining member using a combination of welding and soldering to provide a connection between the pontic and bridge retaining member which is substantially stronger than a soldered connection and which does not require casting in constructing the bridge or, in fact, any individual member of the bridge. Moreover, the method of the present invention makes it much easier to form an acceptable solder connection and with less skill. Welding is not currently practiced in the construction of a crown and bridge since welding causes the base metal to melt whereas in soldering only the solder material is melted.

The method of the present invention is particularly suited to the construction of a dental bridge in which the pontic is united to a prefabricated bridge retainer constructed from relatively thin metal foil without casting. In fact, in accordance with the present invention, neither the bridge retainer(s) nor the pontic need be cast and each may be of a prefabricated construction with relatively little constraint in the amount of metal used or its thickness. The method of the present invention in conjunction with the use of non cast metal bridge retainer(s) eliminates casting from dental bridge construction in its entirety.

A dental prosthesis assembly has also been developed to facilitate the construction of a dental bridge, without casting, from prefabricated metal retainer(s) and a prefabricated pontic. The dental prosthesis assembly of the present invention comprises a metal pontic constructed with an arm rest extending from opposite ends thereof for suspending the pontic between bridge retainers mounted on adjacent abutment teeth to form a bridge therebetween and a metal spacer for joining each arm rest to each corresponding bridge retainer through a welding operation. Each metal spacer is preferably composed of at least several layers having at least one layer of high fusing temperature metal. The metal spacers are adapted to be interposed between each arm rest and each bridge retainer to permit the arm rest to be spot welded to the retainer. The dental prosthesis assembly is modified in accordance with the present invention to form a splint for bracing two or more teeth without casting. In such instance, a pontic is not required and the splint is formed using opposing arm rests extending from a common joint. The arm rests are spot welded to the bridge retainers through the metal spacers.

OBJECTS OF THE INVENTION

Accordingly, it is an object of the present invention to provide a method for constructing a dental bridge without casting.

It is another object of the present invention to provide a method for constructing a dental bridge from prefabricated metal retainers and a prefabricated pontic.

It is a further object of the present invention to provide a method for constructing a dental bridge with the pontic welded to the bridge retainer.

It is an even further object of the present invention to provide a dental prosthesis assembly for forming a dental bridge and a dental splint without casting.

SUMMARY OF THE INVENTION

The foregoing objects are achieved by the method and prosthesis assembly of the present invention.

The method of the present invention for constructing a dental bridge between an abutment tooth or teeth upon which metal retaining member(s) are mounted comprises the steps of: mounting the metal retaining member(s) upon a die prepared from the abutment teeth: fabricating a pontic to fill the edentulous space between the abutment teeth with the pontic having a pliable arm rest extending outwardly from opposite ends thereof; suspending the pontic between the retaining members with each arm rest mounted on the occlusal surface of a retaining member; adjusting the position of each arm rest to establish a desired alignment between said pontic and the abutment teeth; spot welding the arm rest to the occlusal surface of each retaining member to form a welded joint; and soldering the interproximal space between each retaining member and pontic contiguous with each arm rest.

The prosthesis assembly for fabricating a dental bridge to an abutment tooth or teeth upon which metal retaining member(s) are mounted comprises: a metal pontic for filling the edentulous space adjacent the metal retaining member(s), with the pontic having an arm rest extending outwardly from opposite ends thereof for suspending the pontic between the metal retaining member(s) and a metal spacer for each metal retaining member with each metal spacer adapted to be interposed between an arm rest and a corresponding metal retaining member so as to permit each arm rest to be joined to each metal retaining member by spot welding.

DESCRIPTION OF THE DRAWINGS

Comprehension of the invention is facilitated by reading the following detailed description of the invention in conjunction with the following drawing of which:

FIG. 1A is an exploded view in perspective of the prosthesis assembly of the present invention for constructing a dental bridge between two metal retaining members in accordance with the method of the present invention:

FIG. 1B is a perspective view of the assembly of FIG. 1A during the operation of spot welding the pontic to each retaining member;

FIG. 1C is a perspective view of a dental bridge formed in accordance with the present invention from the prosthesis assembly shown in FIGS. 1A and 1B:

FIG. 1D is a magnified view of the cross section of the metal spacer used in the prosthesis assembly of FIG. 1;

DETAILED DESCRIPTION OF THE INVENTION

Figure 2:
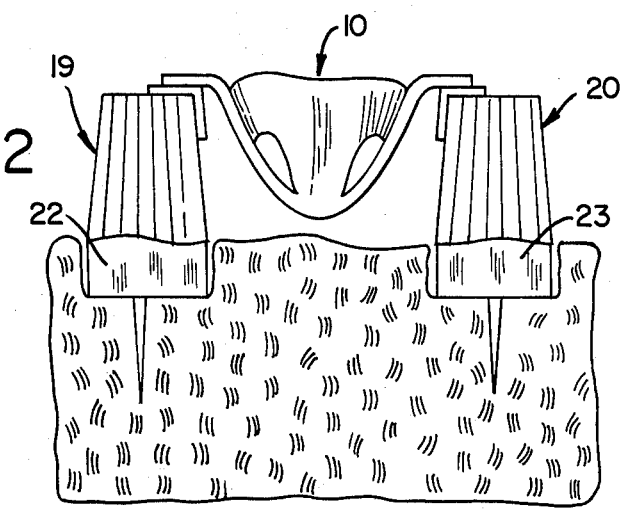
FIG. 2 is a side elevation of the prosthesis assembly of the present invention shown assembled upon two metal retaining members mounted on dies of the abutment teeth for constructing a threeunit pontic bridge in accordance with the present invention.
Figure 3:
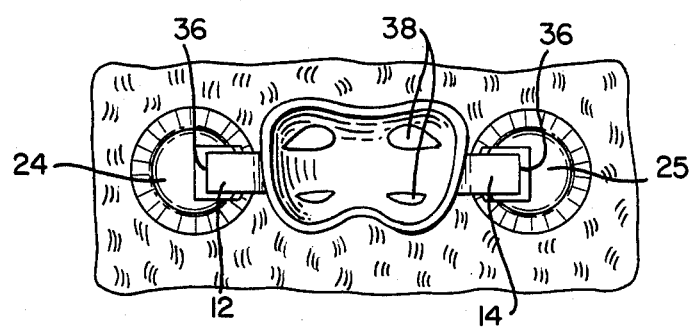
FIG. 3 is a top view of the assembly of FIG. 2.

The prosthesis assembly for constructing a dental bridge in accordance with the present invention is shown in FIGS. 1-3 and comprises, in combination, a metal pontic 10 and metal spacers 16 and 18 respectively. The metal pontic 10 has a shaped body 11 and two arm rests 12 and 14 which extend outwardly from opposite ends of the body 11. The arm rests 12 and 14 permit the pontic 10 to be suspended between the metal retaining members 19 and 20 in the construction of a dental bridge. The metal spacers 16 and 18 are preferably in the form of metal strips which function to reinforce the occlusal surfaces of the metal retaining members to permit the arm rests 12 and 14 to be spot welded to the metal retaining members 19 and 20 for forming a fixed bridge.

The metal retaining members 19 and 20 protect the abutment teeth (not shown) and serve as structural supports in constructing a dental bridge. The abutment teeth of the patient may be prepared for full crown, partial crown or metal inlay. In the construction of a crown, particularly a full crown, the metal retainer is referred to as a metal coping. The design of the metal retainer is not critical to the present invention nor is the configuration or method of construction used in forming the metal retainer critical to the present invention. A metal retaining member for a full crown constructed from a relatively thin metal foil, without casting, is disclosed in U.S. Pat. Nos. 4,273,580, 4,459,112 and 4,492,579, respectively. The metal foil, as taught in the latter two patents, is preconfigured into a geometry with multiple folds or pleats which extend from an unfolded central area defining the occlusal surface of the coping. The multiple folds are folded over one another in a partially overlapping relationship before the foil is adapted to the die.

The metal retaining members 19 and 20 as shown in the drawings of FIGS. 1-3, 6 and 7 are representative of full crown metal copings which are adapted to the respective dies 22 and 23 (FIG. 2) of the abutment teeth using a conventional swaging device as is well known to those skilled in the art and as is elaborated on in the aforementioned U.S. Patents. The metal retaining members 19 and 20 are preferably constructed from a laminated precious metal foil as taught in U.S. patent application Ser. No. 690,650 entitled "Metal Coping and Crown for A Ceramo-Metal Restoration" filed on Jan. 11, 1985 and in U.S. patent application Ser. No. 802,987, entitled "Dental Coping and Crown" filed on Nov. 29, 1985. A prefabricated metal retaining member must be relatively thin regardless of construction so that it can be adapted to the die of the abutment tooth. In general, the thickness of the metal retaining members 19 and 20 are under 150 microns with their occlusal surfaces 24 and 25 generally even thinner, e.g., between 30 and 100 microns.

The metal spacer 16 and 18 are inserted between the arm rests 12 and 14 of the pontic 10 and the occlusal surfaces 24 and 25 of the metal retaining members 19 and 20, respectively. Each of the metal spacers 16 and 18 may be composed of a precious metal gold alloy having a relatively high fusion temperature of at least about 1200° C. but preferably above 1250° C. The preferred construction for each metal spacer 16 and 18 is a laminated composite of multiple metal layers as shown in FIG. 1D. In the arrangement of FIG. 1D each spacer has a central layer 27 of high fusion temperature precious metal such as palladium separated on both sides by a gold or gold alloy layer 28 and 29 with the gold layers 28 and 29 being substantially equal in thickness. Each spacer 16 and 18 is preferably bent to form an elbow 30 and 31 corresponding to the bend in the retaining members 19 and 20 between the occlusal and proximal surfaces respectively. This simplifies mounting the spacers upon the retaining members and provides a depending section 32 and 33 which lies on the proximal side of the retainers. The depending sections 32 and 33 of each spacer provides a surface for readily forming the interproximal solder joints 34 and 35 respectively.

The spacers 16 and 18 have a predetermined thickness based on the thickness of the arm rests to provide an overall thickness of metal measured occlusally from the abutment teeth equal to not more than 500 microns. A suitable thickness for each of the metal spacers 16 and 18 lies between 80-150 microns with about 120 microns optimum. The overall dimensions for the spacers is not critical to the invention. The length and width dimensions of the spacers 16 and 18 need only be sized to cover a relatively small surface area of the occlusal surfaces 24 and 25, as shown in both FIGS. 1C and 3. The surface area delimited by the spacers 16 and 18 should however be slightly larger than the area covered by the arm rests 12 and 14 so as to form a border 36 as shown in FIGS. 1B, 1C and FIG. 3, respectively. The border 36 facilitates mounting the arm rests 12 and 14 without forming an overhang and more importantly causes an increase in the distribution of forces applied through the arm rest over a large occlusal surface area.

Figure 4:
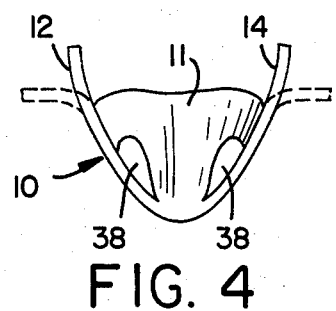
FIG. 4 is a side elevation of the preferred configuration of a molar pontic for use in the prosthesis assembly of the present invention.

The pontic 10 is preferably a prefabricated structure which may be constructed using any conventional manufacturing method including die casting although stamping is preferred. The present invention contemplates the use of any pontic design or configuration for the body 11 with the arm rests 12 and 14 preferably representing relatively thick but pliable extensions which are adapted to be mounted the occlusal surfaces 24 and 25 of the metal retainers 19 and 20 respectively. The arm rest(s) must be sufficiently flexible so that each can be adjusted in position over the retaining members to establish perfect alignment between the abutment teeth and the pontic 10. Moreover, for packaging, stacking and manufacturing purposes it may be desirable to initially have the arm rests 12 and 14 in a generally vertical position as shown in FIG. 4 from which they may be adjusted into a horizontal position as shown in FIG. 1 when constructing a dental bridge. The arm rests should be capable of being bent either with one's hands but preferably requiring a tool such as a pair of pliers. Although pliable, the arm rests 12 and 14 should also provide body and strength. A thickness of between 200-300 microns should provide satisfactory strength and flexibility. The arm rest should also have a width larger than its thickness and preferably between 1-3 mm in width. The thickness of the arm rest, spacer element and the retaining member should be selected not to exceed about 500 microns.

Although the geometry of the body 11 of the pontic 10 is not critical to the present invention it is preferred that the pontic body 11 be designed with a cradle-like shape for a posterior tooth as shown in FIGS. 1-4 in accordance with the principles of construction taught and described in U.S. Pat. No. 4,237,740, the disclosure of which is herein incorporated by reference. As taught in the above mentioned patent, the cradle-like geometry of the pontic body 11 should form a large occlusal concavity 37 which is adapted to be filled with veneer material such as porcelain after the construction of the bridge is completed. The pontic body 11 should have open spaces 38 so that the body 11 functions as a reinforcing structure for the porcelain.

Figure 5:
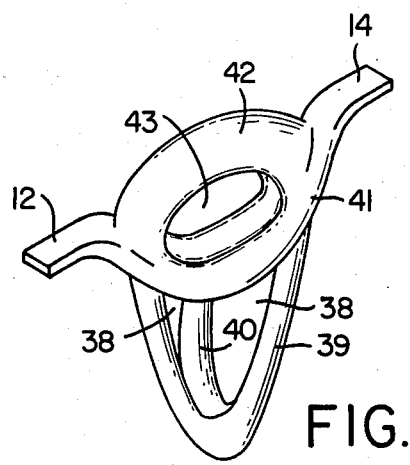
FIG. 5 is a perspective view of the preferred configuration of an anterior pontic for use in the prosthesis assembly of the present invention.

The pontic body 11 for an anterior tooth is preferably designed as shown in FIG. 5. The principles of construction for an anterior pontic is similar to that for a posterior pontic. Open spaces 38 are formed between interconnecting metal members 39 and 40 both on the buccal and lingual sides which form an open framework. The member 39 is looped in the shape of a "U" on the buccal side of the restoration and depends gingivally from a relatively crescent shaped member 41 which lies in a mesial distal plane in the completed restoration. The member 40 joins the member 39 to the crescent shaped member 41 occlusocirvically. The crescent shaped member 41 provides a surface concavity facing the occlusal surface. An additional metal member 42 extends upright from member 41 to form a loop with a space 43. The space 43 forms a porcelain pocket after the veneer material is applied and fired which places the porcelain in compression. The upright member 42 acts as a brace to provide resistance to impact directed at the incisal edge of the anterior tooth. The principles of construction for the anterior pontic is taught in U.S. Pat. No. 4,318,697.

The pontic 10 including its arm rests 12 and 14 may be fabricated from any desired metal composition which meets the standards of compatibility for use in the oral cavity. Accordingly, any conventional precious or semiprecious metal or alloy composition presently known for forming a pontic may be used although a gold alloy is preferred.

The prosthesis assembly is assembled for constructing a dental bridge by mounting the spacers 16 and 18 over the bridge retaining members 19 and 20 as shown in FIG. 1A and 1B. The pontic arm rests 12 and 14 are then placed upon the spacers 16 and 18 over the occlusal surfaces 24 and 25 of the retaining members 19 and 20 respectively, preferably leaving a slight border 36 exposed around the periphery of the arm rests 12 and 14. Each arm rest 12 and 14 may now be spot welded to the retaining members 19 and 20. It is preferred that during the spot welding of one of the arm rests the other arm rest should be held secured to the retaining member upon whih it is seated using a jig or vise such that the alignment of the pontic is maintained during the spot welding procedure. It should be understood that the spot welding operation is carried out on the working model with the bridge retaining members 19 and 20 in place on the respective dies 22 and 23 of the abutment teeth as shown in FIG. 2.

The spot welding operation is carried out using two electrodes 45 and 46 which are held initially against the arm rest 12 in relative close proximity. The electrodes are connected to a welding power supply (not shown). Electric current flows from one electrode to the other through e.g. the arm rest 12, spacer 16 and retaining member 19 causing localized melting which permits the parts to coalesce and form a welded joint 48. Spot welding is a well known welding process applied to relatively thin sheets of metal using electrodes of high conductivity held in contact with the metal to be joined. The electrodes conduct heat from the contact spot until the resistance heat at the contact spot causes the sheets to fuse together. The spacers 16 and 18 permit fusion to occur with the base metal of each retaining member 19 and 20 and without concern for ng a hole in the retag members. The high fusion temperature composition of the metal spacers alloys with the base metal so that the welded joints 48 and 49 will not open during soldering or during porcelain firing. After the arm rest 12 is welded to the retaining member 19 the spot welding operation is carried out between the arm rest 14 and the retaining member 20 to form the welded joint 49.

For maximum strength and rigidity the pontic 10 should be soldered to the retaining members 19 and 20 following the spot welding operations. The solder joint 34 and 35 should be formed in the interproximal space between the pontic 10 and each retaining member 19 and 20 contiguous to each arm rest 12 and 14. The soldering operation is performed directly on the working model by directing solder in each area directly below each arm rest 12 and 14 between each depending section 32 and 33 and the proximal side of the pontic. Forming a soldered joint in combination with the weld joint is preferred to distribute the forces to the interproximal. It is however not critical to the present invention.

The solder composition is also not critical to the present invention. It has, however, been discovered that a fused bond stronger than a conventional solder joint can be formed using a solder composition containing silver chloride (AgCl) above 0.5% but preferably above 3.5% and up to 10%. The solder composition should also contain at least 80% Au and preferably above 90% gold with the remainder, other than AgCl, taken from the group consisting of Pt. Pd and Cu with each up to about 3% although not necessarily of equal amounts. It should be understood that although the expressions "soldering composition" and "solder joint" are used throughout the specification, it is intended to encompass "brazing" and "brazing composition." Soldering and brazing are used in dentistry almost as equivalent terms.

Figure 7:
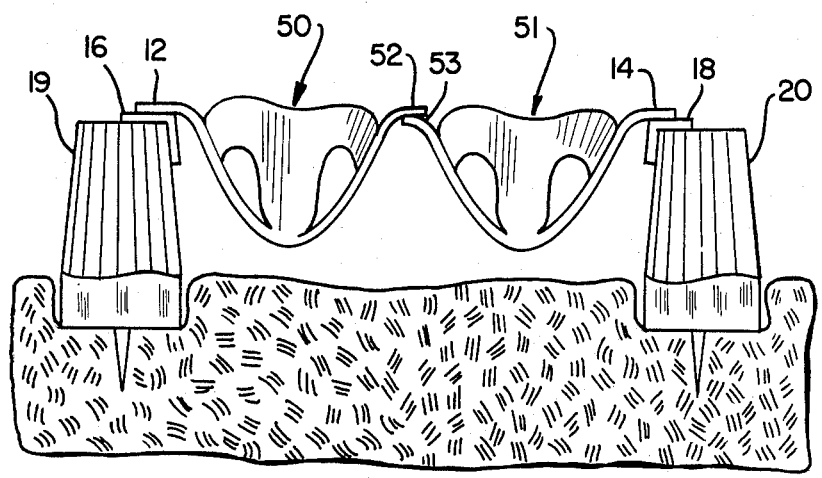
FIG. 7 is a side elevation of a four unit pontic bridge shown assembled in preparation for being joined in accordance with the present invention.
Figure 8:
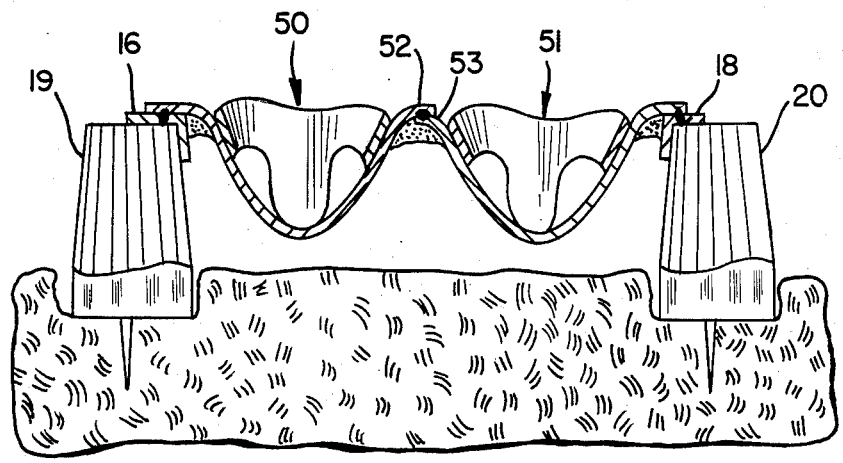
FIG. 8 is a side elevation of the four unit pontic bridge of FIG. 7 joined to the bridge retaining members in accordance with the present invention.

The method and prosthesis assembly of the present invention is shown in FIGS. 1-3 in conjunction with the construction of a typical three unit bridge in which the pontic is supported on both sides by a metal retaining member. The invention is equally applicable to a cantilever bridge with only one retaining member (not shown) and to a four or more unit bridge containing multiple pontics connected in series. A four unit bridge is shown in FIGS. 7 and 8 with the two pontics 50 and 51 connected together by overlapping the arm rests 52 and 53 and welding them together. The two pontics 50 and 51 may also be formed as one integral unit with the arm rests 52 and 53 formed as one solid member. The arm rests 12 and 14 have been given the same reference numbers as their counterparts in FIGS. 1-3 to identify their equivalence. If the arm rests 52 and 53 are welded together as shown in FIG. 8 it is preferred to also solder the welded joint at the interproximal. When pontics are to be joined together, the overlapping arms 52 and 53 should preferably be shortened by cutting the ends so as to make the joint between the pontics stronger.

The method of constructing a four unit bridge is basically no different from that of the three unit bridge shown in FIG. 1-3 once the pontics 50 and 51 have been united. Each of the pontic bodies is identical to the pontic body 11 of pontic 10. The prosthesis assembly for a four unit bridge differs only by an additional pontic from the three unit bridge.

Figure 6:
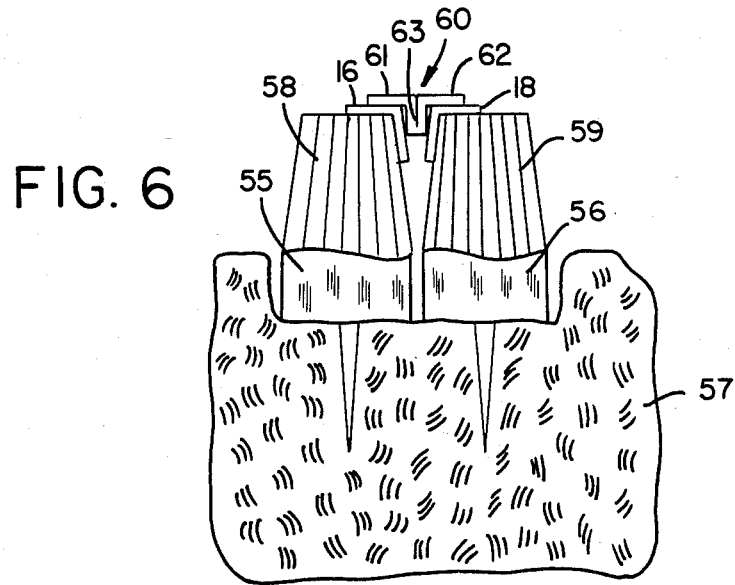
FIG. 6 is a side elevation of the prosthesis assembly of the present invention for forming a splint between adjacent abutment teeth.

The present invention also covers the construction of a splint between adjacent abutment teeth as shown in FIG. 6. A die 55, 56 of each of the abutment teeth (not shown) is formed on a working model 57. A retaining memer 58 and 59 is formed for each abutment, tooth and adapted to each corresponding die 55 and 56 respectively. The retaining members 58 and 59 correspond to the retaining members 19 and 20. The metal splint 60 comprises two metal arm rests 61 and 62 extending from a common joint 63. The arm rests 61 and 62 are seated upon metal spacers 16 and 18 which have been given identical reference numbers to identify their direct correspondence with the spacers for the three and four unit bridges of FIGS. 1-3 and FIGS. 7-8 respectively. The arm rests 61 and 62 correspond to arm rests 12 and 14 and are spot welded to the retaining members 58 and 59 in precisely the same way as shown and described heretofore in connection with the three unit bridge of FIGS. 1-3 and the four unit bridge in FIGS. 7 and 8. However, because of the close proximity of the retaining members 58 and 59 it may not be necessary to form a solder joint at the interproximal.

As earlier stated, it is the principal function of the metal spacers 16 and 18 to reinforce the occlusal surfaces 24 and 25 of the retaining members 19 and 20 to facilitate spot welding the arm rests 12 and 14 to the retaining members. Obviously the spacers can be separately bonded or soldered to the occlusal surface of the retaining member after it is adapted to the die to form a coping with a reinforced retaining member. In such case the arm rest can be directly welded to the reinforced retaining member. Ideally, the retaining member would be manufactured with a reinforced occlusal surface so that the spacer can be eliminated. However, this would make the retaining member less desirable since it would be more difficult to adapt to the die. In either case, the broad concept of the present invention covers suspending a pontic with pliable arm rests between the occlusal surfaces of the retaining members, adjusting the arm rests to align the pontic to the abutment teeth with each arm rest being spot welded to a retaining member with or without a spacer therebetween and soldering the interproximal space between the pontic and each retaining member. The use of the spacers 16 and 18 are however preferred. The prosthesis of the present invention broadly covers a pontic having non-rigid pliable arm rests which extend from opposite ends thereof for attachment to the metal retaining members of abutment teeth with or without a metal spacer. The use of multiple arm rests are taught in the aforementioned parent application Ser. No. 723,072.

What we claim is:

1. A dental prosthesis for constructing a dental bridge to an abutment tooth or teeth, with each abutment tooth having a metal retaining member mounted thereon, comprising: a metal prefabricated pontic having an adjustable arm rest extending from opposite ends thereof, with each arm rest adapted to be mounted on the occlusal surface of a metal retaining member and being pliable and separately adjustable independent of the other arm rest for adjustment into a stationary position in physical contact with each retaining member so as to permit joining of each arm·rest to each metal retaining member by a welding operation.

2. A dental prosthesis as defined in claim 1 wherein each metal spacer comprises at least one layer of a high fusing temperature metal.

3. A dental prosthesis as defined in claim 2 wherein each spacer is composed of a plurality of layers with one layer of high fusing temperature metal and another layer of low fusing temperature metal.

4. A dental prosthesis as defined in claim 3 wherein said low fusing temperature layer is of a gold based composition of up to 100% gold.

5. A dental prosthesis as defined in claim 4 wherein each metal spacer is bent to conform to the shape of the metal retaining member upon which it is seated.

6. A dental prosthesis as defined in claim 5 wherein each bent metal spacer has a depending section adapted to be mounted flush against the proximal surface of the retaining member.

7. A dental prosthesis as defined in claim 6 wherein the thickness of each metal spacer and each arm rest for each retaining member should not exceed about 500 microns.

8. A dental prosthesis as defined in claim 7 wherein the thickness of each metal spacer is between 80–150 microns.

9. A dental prosthesis as defined in claim 6 wherein the length and width dimension of each spacer is sized to provide a border extending beyond the periphery of each arm rest.

10. A dental prosthesis as defined in claims 4 comprising another pontic for forming a four unit bridge.

11. A dental prosthesis as defined in claim 10 wherein the arm rest of each pontic is welded together in an overlapping relationship.

12. A dental prosthesis as defined in claim 1 or 4 wherein said pontic has a shaped body with open spaces.

13. A dental prosthesis assembly as defined in claim 12 wherein said shaped body of said pontic has a cradle-like geometry with an occlusal concavity for forming a posterior restoration.

14. A dental prosthesis assembly as defined in claim 12 wherein said shaped body at said pontic has an open framework of metal members and an upright member for forming an anterior restoration.

15. A dental prosthesis assembly as defined in claim 12 wherein each retaining member mounted on an abutment tooth is formed from a relatively thin metal foil comprising multiple laminated layers of precious metal.

16. A method for constructing a dental bridge to an abutment tooth or abutment teeth with each abutment tooth having a metal retaining member mounted thereon comprising the steps of:
mounting the retaining member(s) upon a die prepared from each abutment tooth or teeth;
fabricating a pontic to fill the edentulous space between the abutment teeth with the pontic having a nonrigid pliable arm rest extending outwardly from opposite ends thereof;
mounting each arm rest upon each retaining member;
adjusting the position of each arm rest to establish a desired alignment between said pontic and said abutment teeth; and
spot welding each arm rest to each retaining member.

17. A method as defined in claim 16 wherein each arm rest is mounted upon the occlusal surface of a retaining member.

18. A method as defined in claim 17 wherein the width of each arm rest is larger than the arm rest thickness.

19. A method as defined in claim 18 wherein the width of each arm rest is between 1–3 mm.

20. A method as defined in claim 18 further comprising the step of soldering the interproximal space between each retaining member and pontic contiguous to each arm rest.

21. A method as defined in claim 20 further comprising the step of interposing a metal spacer between each arm rest and each retaining member.

22. A method as defined in claim 21 wherein each metal spacer comprises a high fusing temperature metal.

23. A method as defined in claim 22 wherein each metal spacer is composed of multiple layers of precious metal with one layer comprising palladium.

24. A method as defined in claim 22 wherein each metal spacer is in the form of a strip of metal which is bent to form one section for mounting on the occlusal surface of the retaining member and another section for disposition against the proximal surface of the retaining member.

25. A method as defined in claim 22 further comprising securing one arm rest in position over a retaining member while welding a second arm rest to another retaining member when forming a multiple unit bridge.

26. A method as defined in claim 25 wherein said pontic is suspended between to retaining members to form a three unit bridge.

27. A method as defined in claim 25 wherein one arm rest of said pontic is mounted upon only one retaining member to form a cantilever bridge with the other arm rest removed.

28. A method as defined in claim 25 wherein said pontic is coupled to a second pontic by overlapping the arm rests therebetween and welding them to form a four unit bridge.

29. A method as defined in claim 25 wherein said soldering operation is carried out with a gold based solder comprising at least 0.5% AgCl.

30. A method as defined in claim 29 wherein said solder comprises between 3.5 to 10% AgCl.

31. A dental prosthesis assembly for constructing a splint between adjacent abutment teeth with each abutment tooth having a metal retaining member mounted thereon, comprising: a first and second arm rest connected together at a common joint from which each arm rest extends, with each arm rest adapted to be mounted on the occlusal surface of one of the metal retaining members and a metal spacer for each abutment tooth with each metal spacer adapted to be interposed between each arm rest and the occlusal surface of each metal retaining member for joining each arm rest to each metal retaining member by a welding operation.

32. A dental prosthesis assembly as defined in claim 31 wherein each metal spacer comprises a high fusing temperature metal.

33. A dental prosthesis assembly as defined in claim 32 wherein each metal spacer is composed of multiple layers with one layer of high fusing temperature metal separated between gold layers.

34. A dental prosthesis assembly as defined in claim 33 wherein each metal spacer and each arm rest should not exceed about 500 microns.

35. A method for constructing a dental splint bridging two adjacent abutment teeth with each abutment tooth having a metal retaining member mounted thereon comprising the steps of:
mounting each retaining member upon a die prepared from each abutment tooth:
fabricating a connector having a first and second arm rest connected together at a common joint from which each arm rest extends;
mounting the first arm rest on one retaining member and the second arm rest on the other retaining member;
interposing a metal spacer between each arm rest and each retaining member; and
spot welding each arm rest to each retaining member through each metal spacer.

36. A method as defined in claim 35 wherein each metal spacer comprises a high fusing temperature metal.

37. A method as defined in claim 36 wherein each metal spacer is composed of multiple layers with one layer of high fusion temperature metal separated between gold layers.

38. A dental prosthesis for constructing a dental bridge to an abutment tooth or teeth, with each abutment tooth having a metal retaining member mounted thereon comprising a preformed metal pontic for filling the edentulous space between abutment teeth and means extending from at least one of the interproximal ends of the pontic for joining the pontic to the metal retainer with said means including a pliable non-rigid metal arm rest adapted to extend over the occlusal surface of said metal retainer and having a width larger than its thickness.

39. A dental prosthesis as defined in claim 38 wherein said pontic has a metal arm rest extending from each opposite end thereof.

40. A dental prosthesis as defined in claim 39 wherein said pontic is a prefabricated metal structure with an open framework of interconnecting metal members.

41. A dental prosthesis as defined in claim 40 wherein said interconnecting metal members form a cradle with an occlusal concavity.

42. A dental prosthesis as defined in claim 1 further comprising a metal spacer adapted to be interposed between each arm rest and each metal retaining member.

* * * * *